(12) United States Patent
Morris et al.

(10) Patent No.: US 9,534,197 B2
(45) Date of Patent: Jan. 3, 2017

(54) BIOMASS PRODUCTION SYSTEM AND APPARATUS

(75) Inventors: Milton Hugh Morris, Weimer, TX (US); Katon Hughes Deal Morris, Weimer, TX (US); John Michael Harris, San Antonio, TX (US); Michael Donavan Jochum, Jr., Weimer, TX (US)

(73) Assignee: ALGETERNAL TECHNOLOGIES, LLC, Weimar, TX (US)

( * ) Notice: Subject to any disclaimer, the term of this patent is extended or adjusted under 35 U.S.C. 154(b) by 351 days.

(21) Appl. No.: 12/855,525

(22) Filed: Aug. 12, 2010

(65) Prior Publication Data

US 2011/0039326 A1 Feb. 17, 2011

Related U.S. Application Data

(60) Provisional application No. 61/233,547, filed on Aug. 13, 2009.

(51) Int. Cl.
*C12M 1/00* (2006.01)
*C12M 3/00* (2006.01)
(Continued)

(52) U.S. Cl.
CPC .............. *C12M 23/40* (2013.01); *C12M 21/02* (2013.01); *C12M 23/06* (2013.01); *C12M 29/04* (2013.01); *C12M 33/22* (2013.01)

(58) Field of Classification Search
CPC ....... C12M 23/06; C12M 23/40; C12M 29/04; C12M 33/22
(Continued)

(56) References Cited

U.S. PATENT DOCUMENTS 2,732,663 A 1/1956 Dewey, II
4,724,214 A 2/1988 Mori
(Continued)

FOREIGN PATENT DOCUMENTS

JP 410108665 A 4/1998

OTHER PUBLICATIONS

G. Burgess et al., "Materials, geometry, and net energy ratio of tubular photobioreactors for microalgal hydrogen production," 16th World Hydrogen Energy Conference (WHEC), Jun. 13-16, 2006, Lyon, France, available at http://solar-thermal.anu.edu.au/wp-content/uploads/WHEC-Burgess-biohydrogen.pdf.
(Continued)

*Primary Examiner* — Nathan Bowers
*Assistant Examiner* — Lydia Edwards
(74) *Attorney, Agent, or Firm* — William H. Holt

(57) ABSTRACT

The present invention is a system for optimizing production of biomass. The system contains one or more growth modules under a shading element that diffuses light. Each of the growth modules has a plurality of vertical growth columns arranged on a bottom manifold. The biomass is grown within a liquid growth medium held within each of the vertical growth columns until it reaches a desired growth. The biomass is then harvested through gravitational flow of the biomass and the liquid growth medium out of the bottom of each growth column. The bottom manifold collects gravitational flow of the biomass and liquid growth media from each growth column and aggregates the output of each individual column into a collective output of the growth module.

13 Claims, 11 Drawing Sheets

(51) Int. Cl.
*C12N 1/12* (2006.01)
*C12M 1/12* (2006.01)
*C12M 1/26* (2006.01)

(58) Field of Classification Search
USPC .......................................... 435/257.1, 292.1
See application file for complete search history.

(56) References Cited

U.S. PATENT DOCUMENTS

| | | | |
|---|---|---|---|
| 5,137,828 | A | 8/1992 | Robinson |
| 6,174,720 | B1 | 1/2001 | Oxley et al. |
| 2003/0059932 | A1 | 3/2003 | Craigie et al. |
| 2004/0110273 | A1 | 6/2004 | Akers et al. |
| 2005/0089993 | A1 | 4/2005 | Boccazzi et al. |
| 2005/0239182 | A1* | 10/2005 | Berzin ................... 435/166 |
| 2007/0289206 | A1 | 12/2007 | Kertz |
| 2008/0155890 | A1 | 7/2008 | Oyler |
| 2008/0160591 | A1 | 7/2008 | Willson et al. |
| 2008/0178739 | A1 | 7/2008 | Lewnard et al. |
| 2008/0274494 | A1* | 11/2008 | Kertz ....................... 435/29 |
| 2008/0286851 | A1 | 11/2008 | Whitton |
| 2009/0011492 | A1 | 1/2009 | Berzin |
| 2009/0047722 | A1 | 2/2009 | Wilkerson et al. |
| 2009/0148931 | A1 | 6/2009 | Wilkerson et al. |
| 2009/0151241 | A1 | 6/2009 | Dressler et al. |

OTHER PUBLICATIONS

John S. Burlew (editor), "Algal Culture: From Laboratory to Pilot Plant," book, Fifth Printing May 1976, Carnegie Institution of Washington Publication, available at http://carnegiescience.edu/publications_online/algal_culture/default.html.

Matthew L. Wald, "For Carbon Emissions, a Goal of Less Than Zero," The New York Times newspaper, Mar. 26, 2008, available at http://www.nytimes.com/2008/03/26/business/businessspecial2/26negative.html?_r=1.

Silke Hemming & Uko Reinders, "Light Diffusion Improves Growth," FlowerTech magazine, Feb. 10, 2007, vol. 10/No. 6, available at http://www.robertmarvel.com/PDF/light%20diffusion.pdf.

The Greenhouse Catalog, "Understanding light from a plants prospective," online publication, date unknown, available at www.greenhousecatalog.com/greenhouse-light.php.

Oilgae, website, date unknown, available at www.oilgae.com.

"Do plants grow faster under certain colors of light?," WikiAnswers online publication, date unknown, available at http://wiki.answers.com/Q/Do_plants_grow_faster_under_certain_colors_of_light.

* cited by examiner

BIOMASS PRODUCTION SYSTEM AND APPARATUS

CROSS REFERENCES TO RELATED APPLICATIONS

This application claims the benefit of U.S. Provisional Patent Application Ser. No. 61/233,547, filed Aug. 13, 2009.

STATEMENT REGARDING FEDERALLY SPONSORED RESEARCH OR DEVELOPMENT

Not applicable

BACKGROUND OF THE INVENTION

Technical Field

The present invention generally relates to the field of alternative energy and the efficient creation of alternative energy resources. More specifically, the present invention relates to a biomass production system and apparatus for producing increased yields of biomass.

Description of the Related Art

Society's practically insatiable appetite for fossil fuel energy is a problem of global proportions and alternative energy sources need to be developed for a variety of reasons. One source of alternative energy can be found in the lipids produced by organisms such as plants, algae, and other photoautotrophic organisms. Photoautotrophic organisms are those that use light to produce energy, most commonly through the photosynthetic process. The lipids are extracted from these organisms through a variety of known processes. Once extracted the lipids are processed for their end use, be it food, pharmaceuticals, or energy products such as biodiesel. In addition, once the lipids are extracted from the organisms, any remaining organic matter can be burned to produce heat energy.

Obtaining alternative energy from living organisms presents a challenge. The amount of lipids produced on a per unit basis is relatively small and attaining large yields of lipids requires a significant number of organisms. Growing a sufficient amount of organisms requires large amounts of space. The challenge is further increased with organisms that require light to produce energy and grow. For example, algae grown on the surface of a pond will only grow to a total depth of about nine inches because light cannot penetrate any deeper. Algae cannot grow in the darkness below this top layer and the liquid beneath is essentially wasted from a production standpoint.

BRIEF SUMMARY OF THE INVENTION

The present invention is directed to an efficient system for growing and harvesting a mass of photoautotrophic organisms, or "biomass," in a liquid medium such as water. The present system not only increases the yield of biomass attainable, it also reduces the energy needs to harvest the biomass. Instead of expending energy to collect biomass from a surface pond, for example, the present invention uses gravitational flow to harvest the biomass.

The present invention utilizes one or more vertical growth columns to hold a volume of biomass grown in a liquid growth medium. The vertical columns are made from a material that allows light to pass through it so the biomass at all depths of the column can receive light for photosynthesis. As such, the biomass can be grown throughout the column and biomass growth is attained throughout depths that would not be possible in a horizontal system such as a pond. By extension, more biomass can be produced on the same area of land as compared to horizontal systems.

The verticality of the growth columns also allows the power of gravity to be harnessed for harvesting of the biomass. The biomass is harvested by draining the liquid growth medium—with the biomass contained in it—out of the growth columns. One or more valves located downstream from the gravitational flow of the biomass are opened to initiate a harvest and closed to stop the harvest. A number of vertical growth columns are preferably arranged as a growth module. Each growth module has a bottom manifold for aggregating the output of the columns into a collective output of the growth module. The collective output discharges from the growth module to a harvest tank, a pipeline, or elsewhere for processing.

The present invention also has certain features to stimulate growth of the biomass so that harvest can be achieved more often. For example, the invention has elements to deliver critical gases such as carbon dioxide to the biomass as well as nutrients for growth. In addition, the overall system contains a shading element that creates diffused light for the biomass to absorb because diffused light provides a better growing environment and further increases production

DETAILED DESCRIPTION OF THE INVENTION

Figure 1:
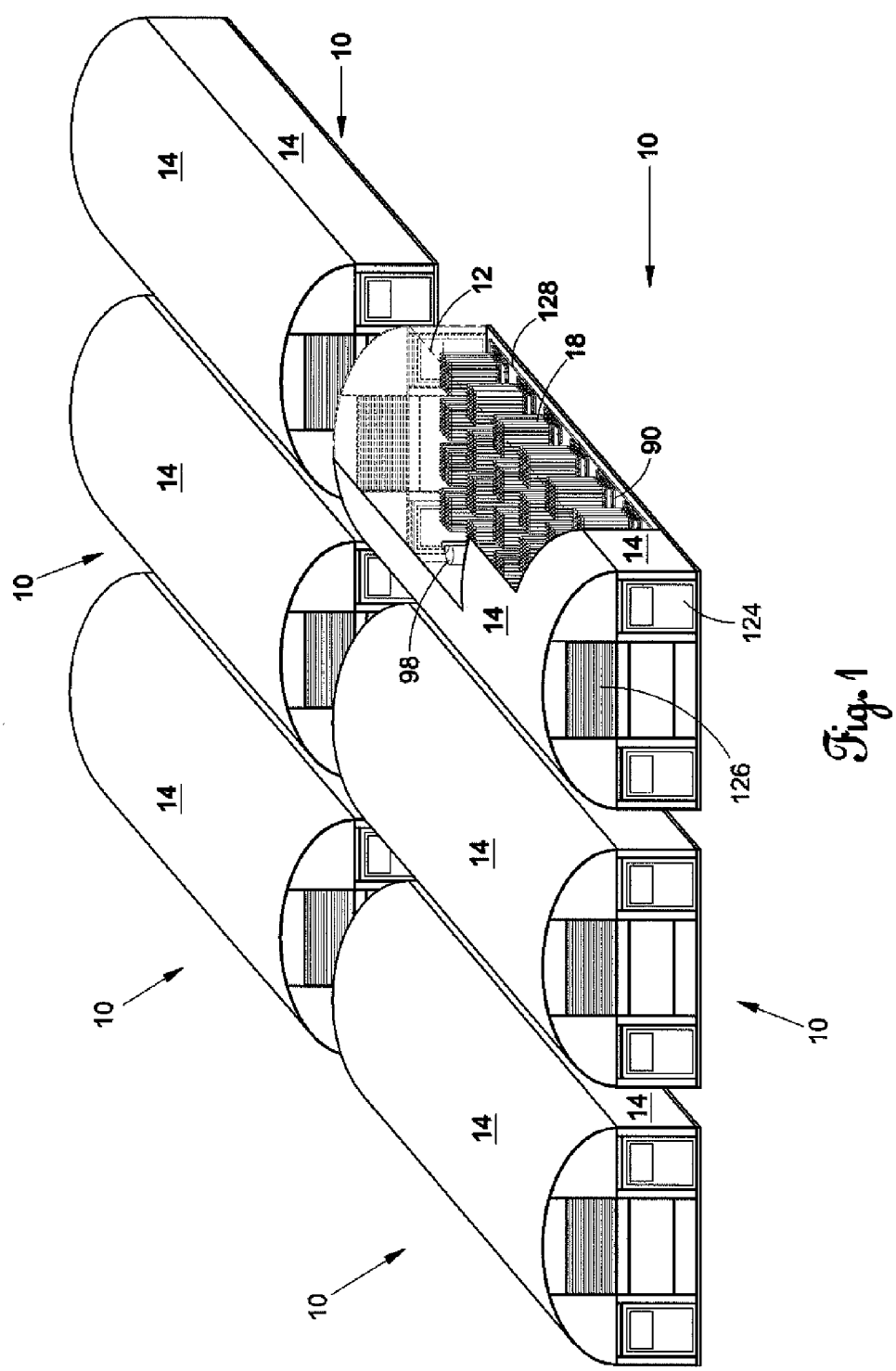
FIG. 1 illustrates a perspective view of a site with several systems for growing biomass, with a portion of the shading element of one of the systems cutaway.

FIG. 1 illustrates a site containing the preferred embodiment of a system 10 for growing biomass in a liquid growth medium (not shown). As shown, the site contains several systems. The system 10 comprises a structure 12 that supports a shading element 14 with the shading element 14 at least partially surrounding a growth column 16 (see FIG. 2). As will be seen, the growth column 16 holds a liquid growth medium in which the biomass grows. The liquid growth medium is anything that allows growth of the biomass such as water, water combined with nutrients, or other types of liquid media. During growth, the biomass is suspended, mixed, or otherwise combined with the growth medium and, together, the biomass and the liquid growth medium are collectively referred to herein as the "biomass/growth medium mixture." The preferred biomass is an algae strain known as *chlorella minutissima*, specifically, the UTEX No. 2219 strain from the University of Texas Culture Collection of Algae, but the biomass can be any mass of photoautotrophic organisms.

As discussed in more detail infra, the system 10 preferably contains a number of growth columns arranged in one or more growth modules. A growth module 18 contains a predetermined number of growth columns arranged in a substantially vertical orientation within the growth module 18 (see FIGS. 1 & 5).

Figure 2:
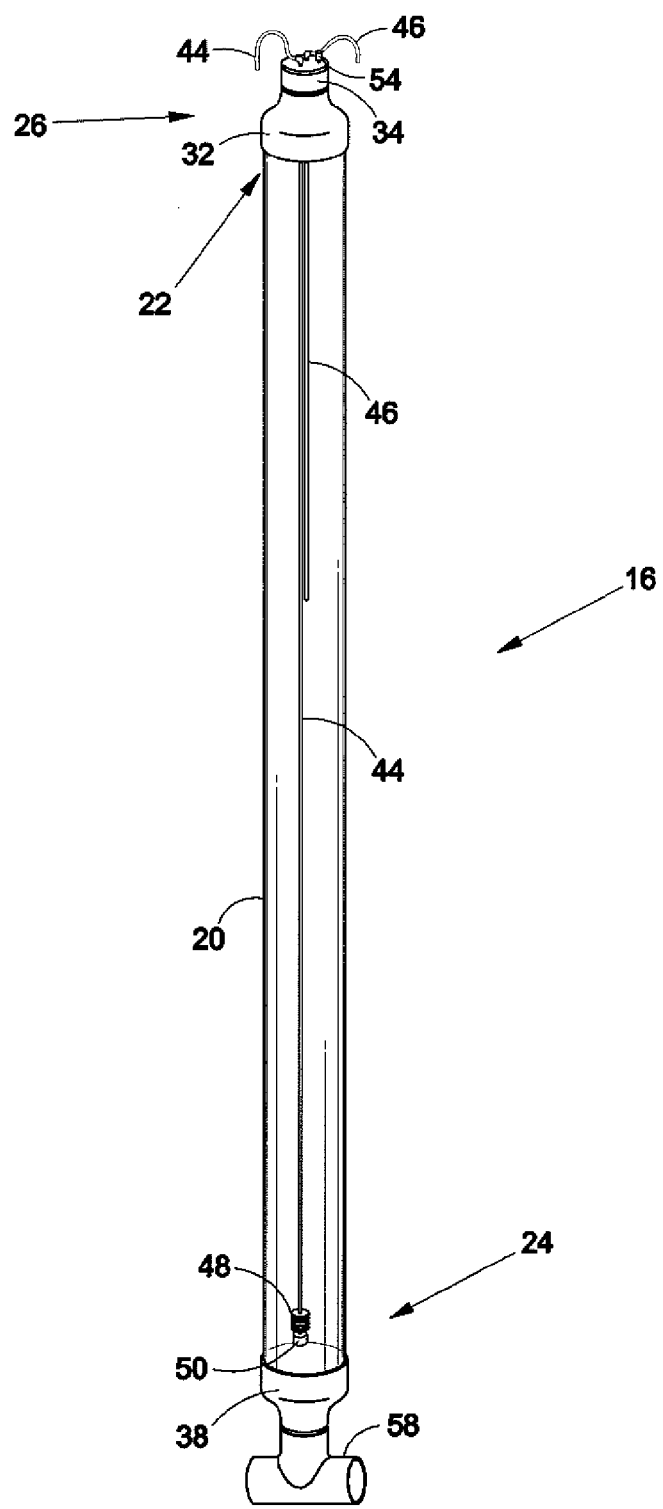
FIG. 2 shows a perspective view of the preferred embodiment of the growth column of the present invention.

Referring to FIG. 2, the preferred embodiment for the growth column 16 is shown. The growth column 16 has a body 20 that is elongated and hollow. Preferably, the body 20 is a circular cylinder (i.e., a tube); however, other elongated hollow bodies (e.g., a tube with a square side profile, an elliptical cylinder, etc.) could be used. The elongated dimension of the body 20 terminates in a top end 22 and a bottom end 24, and the force of gravity is directed from the top end 22 to the bottom end 24.

The body 20 of the growth column 16 is at least translucent and preferably transparent because light must be able to pass through the body 20 of the growth column 16 to the biomass. Preferably, the body 20 is made from transparent polyvinyl chloride (PVC) but could be made from a number of other materials (e.g., glass). The material from which the body 20 is made may be "doped" with an ultraviolet (UV) stabilizer to reduce the amount of UV light which reaches the biomass and to protect the body 20 against degradation from the UV light. Concerning the biomass, research has shown that excessive ultraviolet radiation contained in ultraviolet light can damage photoautotrophic organisms; therefore, a reduction in ultraviolet light may be desirable depending on the particular biomass inside the growth column 16.

Another variant for the body 20 of the growth column 16 is coloration. While the body 20 material may be clear in some embodiments, it could also have a colored tint to it. Adding a colored tint to the body 20 causes filtration of light wavelengths (i.e., colors) because only wavelengths of visible light which match the colored tint will pass through. For example, a red-tinted body 20 allows only red wavelengths of light to pass through the body 20 to the biomass.

Whether the body 20 has a colored tint to it and the coloration of the tint again depends on the needs of the particular biomass. Research shows that unicellular microorganisms similar to the preferred biomass absorb red light and blue light better than other colors in the visible light spectrum. In addition, tests performed on the preferred biomass suggest that this type of biomass prefers red light because an increased yield was shown when red light is used.

The size of the body 20 is another factor of the growth column 16 that can be varied to promote optimal light absorption and therefore increase yield. The size of the side profile affects the amount of light which penetrates to the center of the body 20 and thus, the overall photosynthetic efficiency of the biomass in the growth column 16. If the side profile is too large, not enough light will reach the center of the biomass, thus decreasing optimal photosynthesis.

The preferred size of the side profile varies again according to the needs of the particular biomass, as well as the shape of the side profile. In the preferred embodiment of the growth column 16 with the preferred biomass, the side profile of the body 20 has a six inch diameter. Research concerning algae photosynthesis combined with tests directed to the present system 10 lead to the conclusion that optimal light penetration is achieved from the circumference of the body 20 up to three inches deep. As a result, the circular side profile of the preferred body 20 has a three inch radius, thus making the preferred body six inches in diameter.

Figure 3:
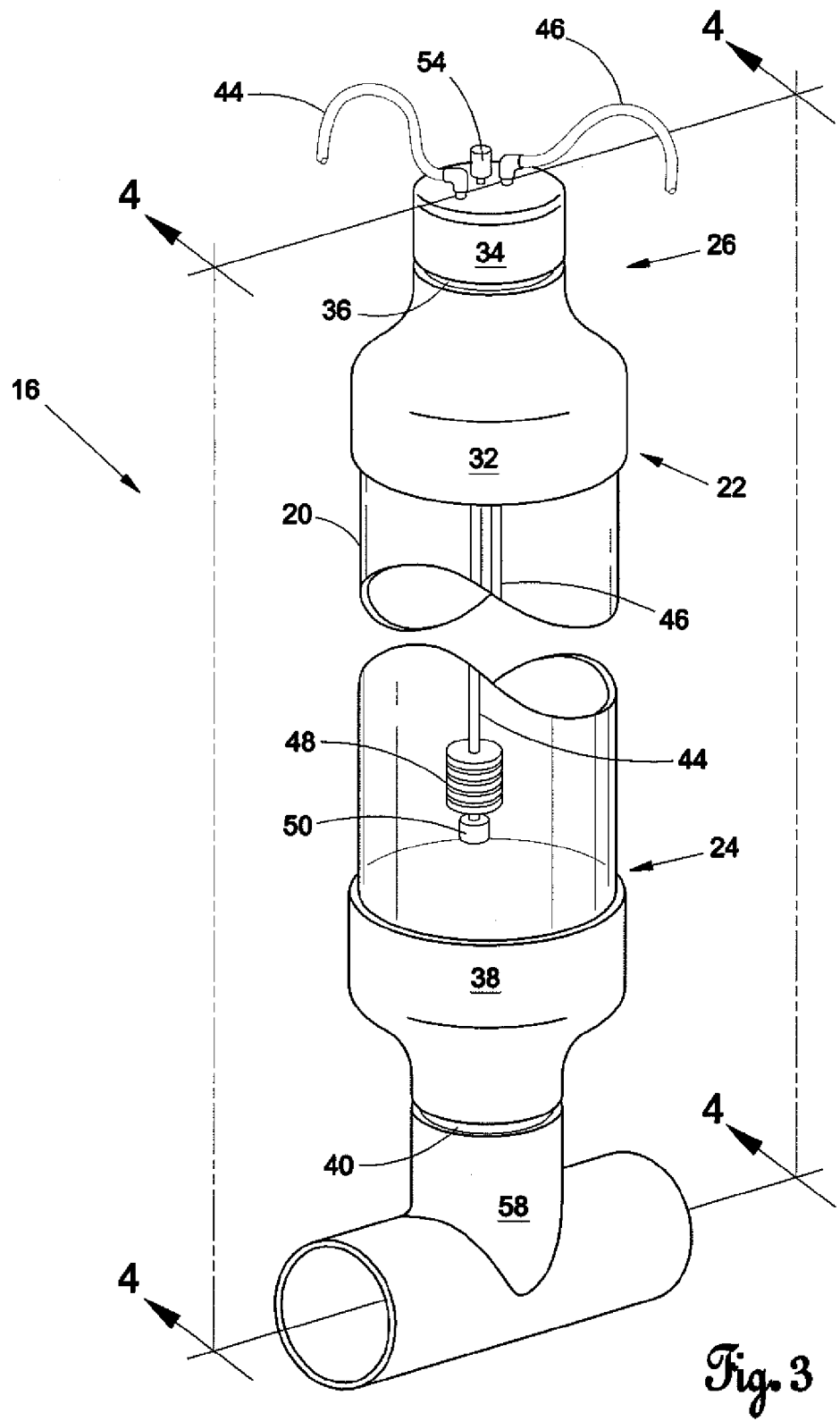
FIG. 3 is an enlarged view of the preferred growth column of the present invention with a portion of the growth column removed.
Figure 4:
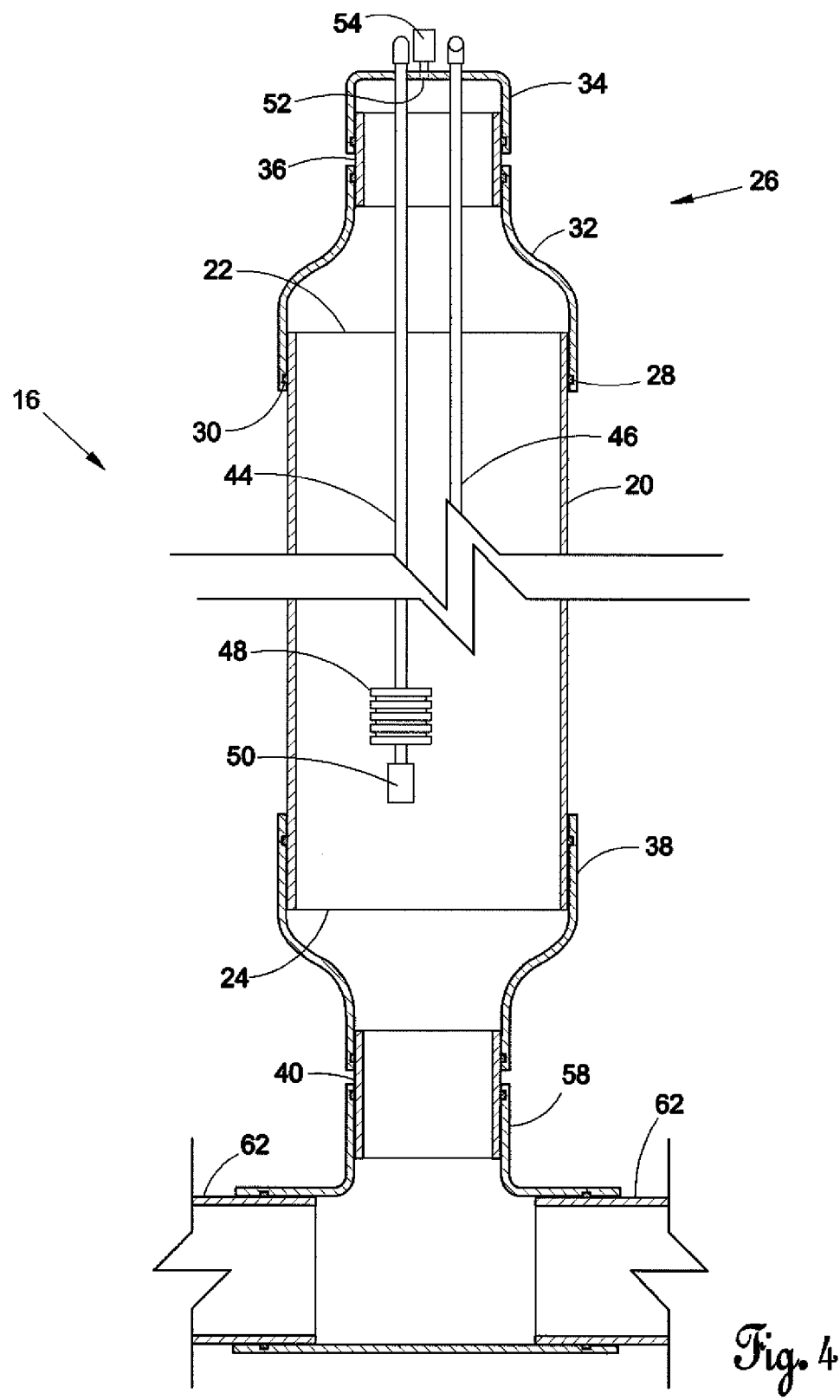
FIG. 4 is a cross-section of FIG. 3 taken along section line 4-4.

The top end 22 of the body 20 is open and connected to the top end 22 of the body 20 is a top piece 26 which covers the opening. As shown in FIGS. 3 & 4, the top piece 26 is preferably a separately manufactured piece that the top end 22 of the body 20 fits within. Alternatively, the top piece 26 could be separately manufactured and fit within the opening at the top end 22 of the body 20, or, the top piece 26 may even be manufactured as part of the body 20.

The top piece 26 preferably connects to the top end 22 of the body 20 with a friction fit and not an interference fit. Although an interference fit may be used in some embodiments, the preferred embodiment does not utilize such a fit because of their tendency to become stuck or frozen together, which creates difficulty when trying to disconnect the connection. Unless otherwise noted, all connections in the growth column 16 and/or the growth module 18 are preferably a friction fit.

A friction fit is achieved when the inner perimeter of the top piece 26, or an element within the top piece 26, contacts the top end 22 of the body 20 but neither the top end 22 nor the body 20 are deformed. During installation of the top piece 26 on the top end 22, the top piece 26 slides adjacent to the outer perimeter of top end 22 but neither perimeter is deformed. In order to achieve a friction fit, at least a portion of the inner perimeter of the top piece 26—or elements therein—is shaped substantially similar to and slightly larger than the outer perimeter of the top end 22 of the body 20. For example, the inner circumference of the top piece 26 is slightly larger that the outer circumference of the top end 22 in the preferred growth column 16.

Preferably, the friction fit connection is sealed from the outside environment with a sealing apparatus. As shown in FIG. 4, an elastomeric O-ring 28 sitting within a groove 30 is the preferred sealing apparatus for the various connections in the invention. The elastomeric O-ring 28 is deformed and presses against a connecting surface to seal the connection and creates friction. For example, the O-ring 28 is deformed by the outer perimeter of the top end 22 of the body 20 when the top piece 26 is installed on the top end 22, thereby causing the O-ring 28 to press against the outer perimeter of the top end 22 and the groove 30 in the inner perimeter of the top piece 26. It should be noted, however, that other sealing apparatuses (e.g., an elastomeric sealing boot) may be used to seal a friction fit connection.

The preferred embodiment of the top piece 26 has three main parts: a top reducer 32, a top cap 34, and a spacer 36. The top reducer 32 decreases the size of the inner perimeter of the top piece 26 as it extends away from the body 20 so that, for example, the inner circumference of the top piece 26 is reduced from approximately six inches in diameter to four inches in diameter as the top piece 26 extends away from the preferred body 20. The spacer 36 connects to the reduced dimension of the top reducer 32 at one end and connects to the top cap 34 at its other end. The top cap 34 terminates the top piece 26.

The top piece 26 helps prevent entry of unwanted items such as harmful bacterial strains or parasitic matter such as fungi into the biomass/growth medium mixture and also it helps prevent evaporation of the liquid growth medium from the growth column 16. It is not required, however, that the top piece 26 create an absolute airtight or even watertight seal. In fact, the top piece 26 has different passageways through it for introducing items to the biomass/growth medium mixture in the growth column 16, as discussed infra.

The bottom end 24 of the body 20 also has a bottom piece 38 connected to it. The bottom piece 38 may be a separately manufactured piece that is installed on the bottom end 24 or may be manufactured as part of the body 20. Preferably, the bottom piece 38 is a separately manufactured piece that is connected to the bottom end 24 of the body 20 with the friction fit and O-ring 28 like the top piece 26, but, unlike the top piece 26, the connection of the bottom piece 38 to the body 20 needs to be sufficiently sealed to prevent liquid growth medium from leaking out of the growth column 16. In its preferred form, the bottom piece 38 is a reducer and its inner perimeter decreases as it extends away from the body 20. So, for example, in the preferred embodiment of the growth column 16, the inner perimeter of the bottom piece 38 decreases from approximately six inches down to four inches. Alternatively, the bottom piece 38 may provide a greater or smaller size reduction ratio or no size reduction at all.

The biomass is harvested through gravity and travels through the bottom piece 38 toward its ultimate destination. When the growth column 16 is used as a standalone, the bottom piece 38 connects to a valve (not shown) that can be opened and closed to activate flow of the biomass/growth mixture out of the bottom piece 38. When the valve is opened, gravity causes the biomass/growth medium mixture to travel from the body 20 of the growth column 16 through the bottom piece 38 and out of the valve, thereby emptying at least a portion of the biomass/growth mixture from the growth column 16. The valve is thus located downstream of the biomass/growth medium mixture flow out of the bottom piece 38. When the growth column 16 is one of many growth columns within the growth module 18, the bottom piece 38 connects through a spacer 40 to a bottom manifold 42 (see FIGS. 5 & 6) and the downstream valve is within the bottom 42 manifold and/or elsewhere, as is discussed in more detail infra.

Extending from the top end 22 of the body 20 toward the bottom end 24 of the body 22 are a gas delivery line 44 and a nutrient delivery line 46. Preferably, the gas delivery line 44 and the nutrient delivery line 46 extend through and protrude from the top piece 26 of the growth column 16; however, they could enter into the cavity of the body 20 in another location other than at the top end 22 (e.g., through the side of the body 20). Within the cavity of the body 20, the gas delivery line 44 preferably terminates near the bottom end 24 of the body 20 while the nutrient delivery line 46 preferably terminates closer to the top end 22 of the body 20. In the preferred embodiment, the gas delivery line terminates approximately two inches from the bottom end 24 of the body 20 and the nutrient delivery line 46 terminate approximately four to six inches from the top end 22 of the body 20.

The gas delivery line 44 delivers predetermined types of gas to the interior of the growth column 16. The gas is forced into the gas delivery line 44 and delivered to the interior of the growth column 16 with pressure. Often, the gas will come from a pressurized storage vessel such as a gas cylinder; however, other means of delivery (e.g., a compressor) could be used. Which gas and the amount of gas delivered typically depends on the particular needs of the biomass growing inside the growth column 16 and, usually, increasing the yield of biomass is the main factor driving gas selection and amount. However, other factors may come into play. For example, a gas may be selected to kill the biomass if a harmful bacterium has been introduced and eradication is desired.

One type of gas that is needed by all types of photoautotrophic organisms is carbon dioxide or $CO_2$. Carbon dioxide is an integral component of photosynthesis. It combines with water ($H_2O$) in the presence of light to form glucose ($C_6H_{12}O_6$) according to the following equation:

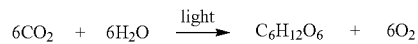

$$6CO_2 \;+\; 6H_2O \;\xrightarrow{\text{light}}\; C_6H_{12}O_6 \;+\; 6O_2$$

The resulting glucose is ultimately absorbed by the organism and converted into cellular constituents, thus allowing growth of the organism.

Delivery of $CO_2$ through the gas delivery line 44 promotes photosynthesis and thus increases the yield of biomass. The amount of $CO_2$ delivered to obtain optimal yield can be correlated to the particular needs of the biomass using growth factors such as the pH level of the growth medium inside the growth column 16. The pH level is measured with a pH meter and adding $CO_2$ makes the growth medium more acidic. With the preferred biomass, for example, it has been found that 7.4 pH is the desired, average pH level of the growth medium in the growth column 16. To attain this level, pure $CO_2$ is delivered to the biomass/growth medium mixture via the gas delivery line 44 at a rate of 20 Liters per minute for 2-5 minutes, until it reaches 6.7 pH. Once the desired pH is reached, the gas delivery is shut off. As the biomass consumes $CO_2$ during photosynthesis, the growth medium becomes more basic and requires additional $CO_2$. It has been found that delivering the $CO_2$ at the above described rates twice a day obtains the desired average.

The gas delivery process can be automated or manually controlled, depending on the complexity of the system 10. For example, valves (not shown) placed between the gas source and the gas delivery line 44 could be manually controlled or automated. Manual control requires periodic testing of the environment within the growth column 16 and manually activating (e.g., physically turning a valve, pressing a button, etc.) the gas delivery based on these values. In an automated system, the delivery rates would be preset into a computer or tied to sensors, such as the pH meter discussed above, that provide real-time feedback of the growing conditions.

Uniform distribution of the gas delivered to the biomass/ growth medium mixture is desirable. To help achieve this goal, the gas delivery line 44 preferably has a weight 48 attached to it just above its termination point within the body 20. The weight 48 helps hold the termination point of the gas delivery line 44 near the bottom end 24 of the body 20. Having the termination point near the bottom end 24 allows the gas to bubble upward through the biomass/growth medium mixture in the body 20 of the growth column 16. In the preferred embodiment the weight 48 is a circular cylinder weight which weighs 42.6 grams, has a 1⅛" diameter, and 1¾" height.

To further increase uniform distribution of gas throughout the biomass/growth medium mixture, the gas delivery line 44 also preferably has a dispersion element 50 connected at its termination point in the body 20. The dispersion element 50 is a porous structure which receives gas from the gas delivery line 44, disperses the gas throughout its pores, and releases the gas from its pores into the biomass/growth medium mixture. The size of the pores in the dispersion element 50 affects the size of gas bubbles released from it, with gas bubbles tending to be smaller in a dispersion element 50 with smaller pores. The preferred dispersion element 50 is a sintered brass product with a ten micron filtration pore size; however, it could be a variety of other products such as a ceramic frit or even a sponge.

The nutrient delivery line 46 delivers liquid-based nutrients and other liquid-based items to the interior of the growth column 16. Liquid-based nutrients fertilize growth of the biomass. The nutrients are suspended, mixed, or otherwise combined in a liquid such as the growth medium or some other type of liquid and flow through the nutrient delivery line 46. In the preferred embodiment, the liquid/nutrient combination discharges from the nutrient delivery line 46 near the top end 22 of the body 20 and gravity helps the liquid/nutrient combination flow from the top end 22 of the body 20 toward the bottom end 24.

Nutrients can be a variety of substances such as, for example, nitrates, ammonia, phosphorous, and potassium. The exact nutrient composition depends on the needs of the particular biomass taking into account factors such as the type of biomass, the growth phase of the biomass, and the desired production of lipids from the biomass. For example, the nutrient needs of the biomass may vary depending on whether the biomass is being initially inoculated into the growth column 16, whether the biomass is being maintained between harvests, or whether the biomass is being replenished after harvest.

In addition to nutrients, the nutrient delivery line 46 may be used to fill the growth column 16 with the biomass/growth medium mixture or the growth medium alone. For example, at initial inoculation, the growth column 16 may be filled with a predetermined ratio of liquid growth medium and biomass by pumping the liquid growth medium and biomass through the nutrient delivery line 46. The nutrient delivery line 46 can also be used to replenish the growth column 16 with liquid growth medium or with additional biomass/growth medium mixture after harvest.

Also shown in FIG. 4, the top piece 26 also has an air delivery passage 52 extending through it. The air delivery passage 52 is a passageway that allows air to travel from the environment outside the growth column 16 to the interior of the growth column 16 and vice versa. Air enters the growth column 16 through the air delivery passage 52 when the biomass/growth medium mixture is harvested and without it, a vacuum would be formed within the growth column 16. In this regard, air travels through the air delivery passage 52 to replace the volume of space formerly occupied by the biomass/growth medium mixture during harvest. Similarly, air passes from the interior of the growth column 16 back to the environment outside the growth column 16 as matter (e.g., nutrients, growth medium, etc.) is introduced to the interior of the growth column 16.

Preferably, a filtering element 54 is located on the top piece 26 where the outside air enters into the air delivery passage 52 so that the outside air must travel through the filtering element 54 prior to entering the air delivery passage 52. Alternatively, the filtering element 54 could be located elsewhere, such as inside the growth column 16 between the air delivery passage 52 and the biomass/growth medium mixture. The filtering element 54 prevents unwanted objects from being introduced to the biomass/growth medium mixture and is chosen according to desired filtration requirements. The preferred filtering element 54 is the same as the preferred dispersion element 50 discussed above and provides a ten micron filtration.

Figure 5:
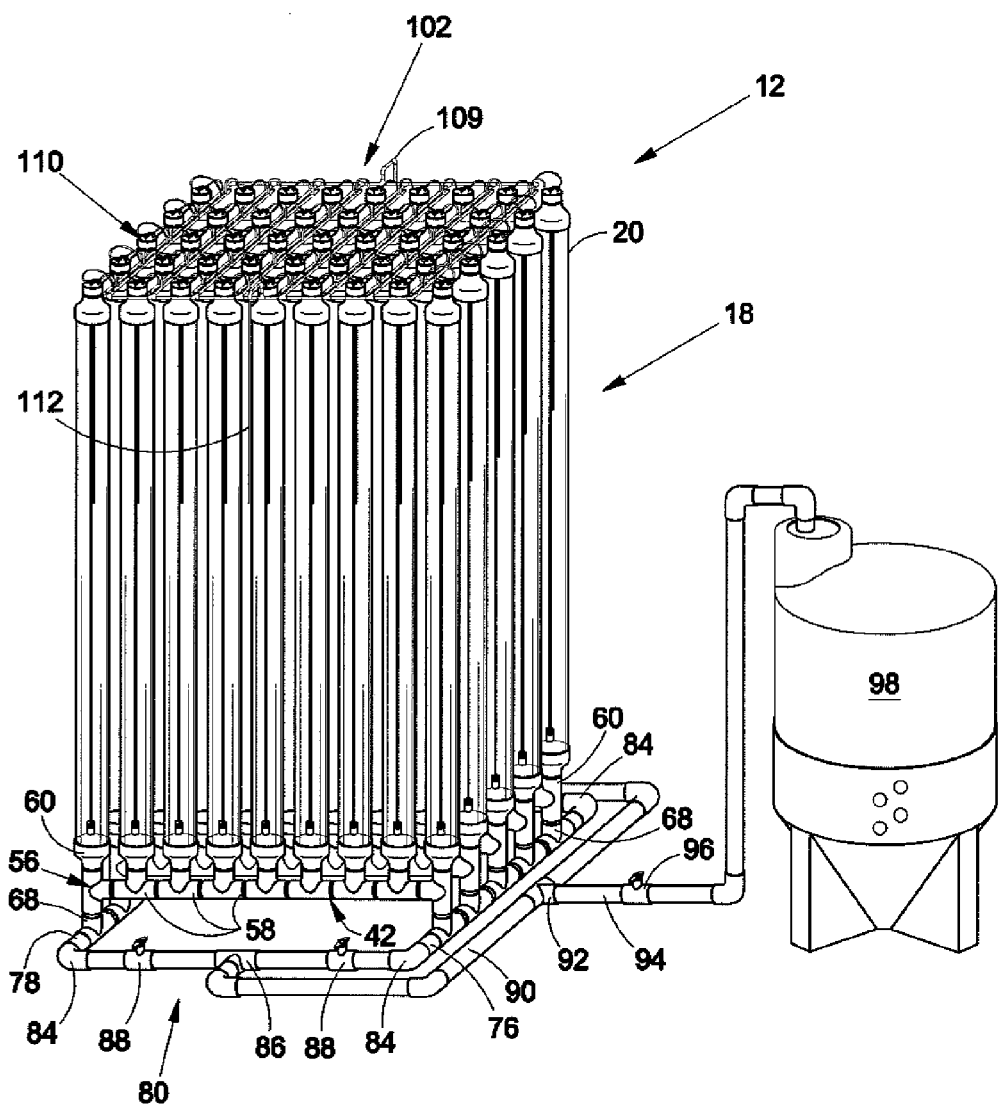
FIG. 5 is a perspective view of the preferred embodiment of a growth module of the present invention and depicts the growth module connected to a harvest tank.

Turning now to FIG. 5, the preferred embodiment of the growth module 18 containing numerous growth columns is shown. Each growth column 16 in the growth module 18 is oriented in a substantially vertical direction and connects to the bottom manifold 42. The bottom manifold 42 is structurally configured to receive the biomass/growth medium mixture from of each growth column 16 in the growth module 18 and to aggregate the collected biomass/growth medium mixture into a collective output (not shown) of the growth module 18. The collective output of the growth module is discharged from the bottom manifold 42 at one or more outlet ports, as discussed below.

Figure 6:
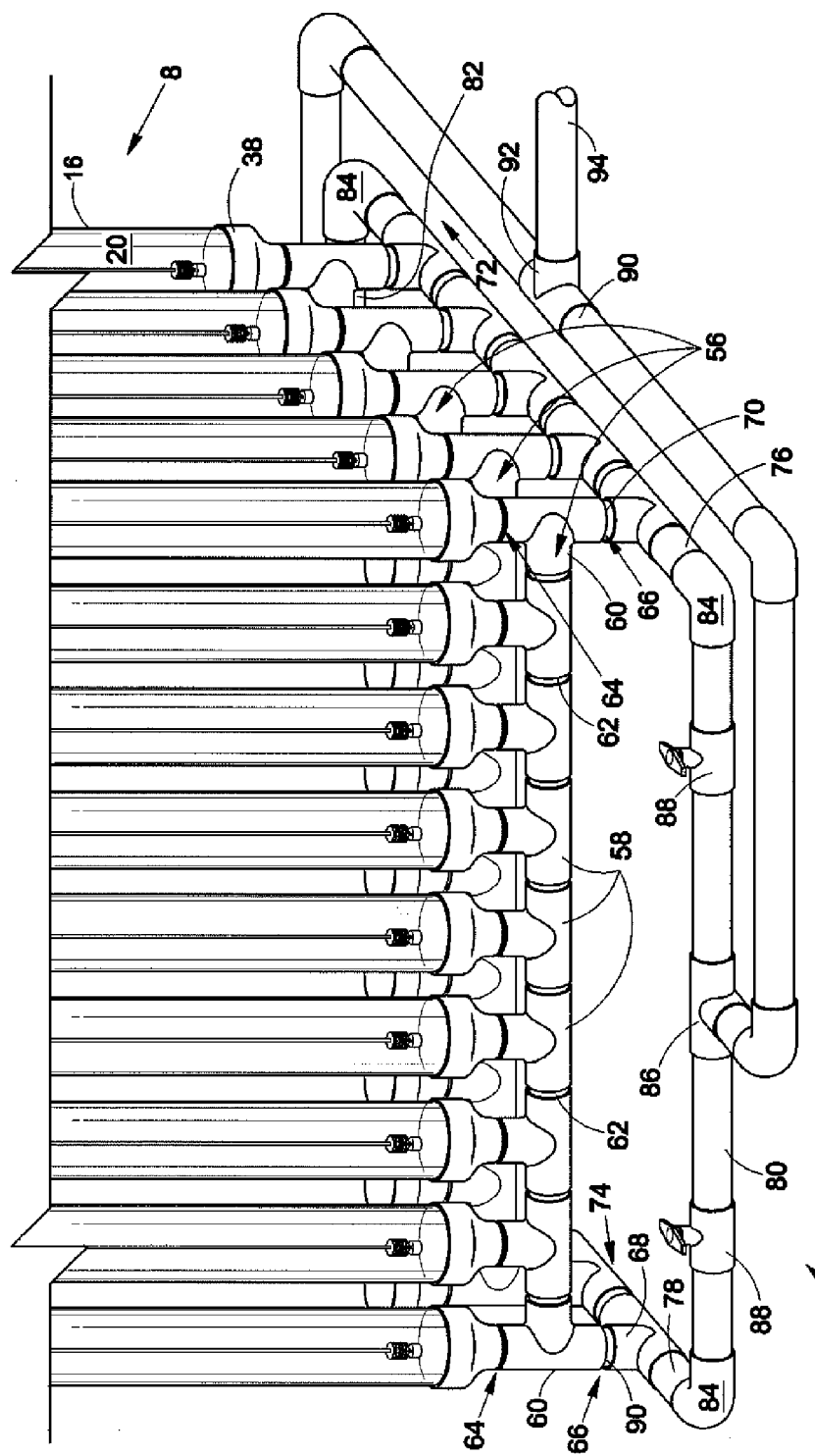
FIG. 6 is an enlarged view of the bottom portion of the growth module depicted in FIG. 5 and shows the preferred embodiment of a bottom manifold.

The design of the bottom manifold 42, which can be varied from that shown, dictates the arrangement and number of growth columns in the growth module 18. In FIG. 6, the preferred embodiment of the bottom manifold 42 is shown for when collective output of an individual growth module 18 is desired. As shown, each growth column 16 is aligned in a manifold row 56 with nine individual growth columns per each manifold row 56. There are five manifold rows per each growth module 18, thereby making a total of forty-five individual growth columns in the preferred growth module 18. The body 20 of each growth column 16 is a minimum distance of 2¾" away from the body 20 of the closest growth columns in the growth module 18, however, this distance could be reduced further depending on the availability of custom manufactured parts.

The bottom piece 38 of each growth column 16 in the preferred growth module 18 connects to the manifold row 56 through either an upper T-joint 58 or an end T-joint 60, depending on the location of the growth column 16 in the growth module 18. Each manifold row 56 is the same length as the other manifold rows in the growth module 18, is aligned substantially parallel to the other manifolds rows in the growth module 18, and is in the same general horizontal plane as the other manifold rows in the growth module 18. The endpoints of each manifold row 56 are also commonly aligned with the endpoints of the other manifold rows in the growth module 18, and, if a plane were laid across the outer edge of the end T-joints at one side of the growth module 18 the plane would touch the outer edge of each end T-joint 60 on that side.

Each upper T-joint 58 in each manifold row 56 is connected in a series with the other upper T-joints in that manifold row 56 with a spacer 62 such that the two aligned openings of each upper T-joint 58 in that manifold row 56 are horizontal. The two aligned openings of the upper T-joint 58 are the two openings of the joint that form a straight passageway through the joint. The other opening of the upper T-joint 58, which is the non-aligned opening, faces vertically upward, toward the individual growth column 16 above the upper T-joint 58. The bottom piece 38 of each growth column 16 that is above an upper T-joint 58 connects to the non-aligned opening of its respective upper T-joint 58 through the spacer 40 (see FIG. 4).

Each manifold row 56 terminates at the end T-joint 60. The non-aligned opening of the end T-joint 60 faces inward, toward the interior of the growth module 18 and both ends of each manifold row 56 are connected to the non-aligned end of their respective end T-joint 60. The two aligned openings of each end T-joint 60 are vertically aligned with the individual growth column 16 above that end T-joint 60. Each end T-joint 60 has an upwardly facing aligned opening 64 and a downwardly facing aligned opening 66 that together form a straight passageway through the end T-joint 60. The upwardly facing aligned opening 64 faces toward the bottom piece 38 of the individual growth column 16 above that end T-joint 60, while the downwardly facing aligned opening 66 faces away from the growth column 16 above that end T-joint 60. The bottom piece 38 of each growth column 16 that is above an end T-joint 60 connects to the upwardly facing aligned opening 64 of its respective end T-joint 60 through the spacer 40 (see FIG. 4).

The downwardly facing aligned opening 66 of each the end T-joint 60 in the preferred bottom manifold 36 faces toward a corresponding lower T-joint 68 located below that individual end T-joint 60. Each end T-joint 60 connects to the non-aligned opening of its respective corresponding lower T-joint 68 through a spacer 68. Because each manifold row 56 terminates with the end T-joint 60 at its two endpoints, two different series of corresponding lower T-joints are formed: a first series 72 of lower T-joints along the endpoints of the manifold rows at one side and a second series 74 of lower T-joints along the endpoints of the manifold rows at the other side.

The two aligned openings of each lower T-joint 68 in a series are aligned with the other aligned openings of the other lower T-joints in that series so that a straight passageway through the lower T-joints is formed. The aligned openings between the lower T-joints in the first series 72 are connected via spacers and the outer lower T-joints in the first series 72 are extended to form a first bottom conduit 76. Similarly, the aligned openings between the lower T-joints in the second series 74 are connected via spacers and the outer lower T-joints in the second series 74 are extended to form a second bottom conduit 78.

The first and second bottom conduits 76 and 78, respectively, in the preferred bottom manifold 42 are substantially parallel to each other. Both also extend horizontally in a direction transverse to the direction of each manifold row 56 extend past the vertical plane formed by the outer edge of the body 20 of the growth columns.

The endpoints of the first and second bottom conduits 76 and 78 connect to each other, as shown in FIGS. 5 & 6 when the preferred bottom manifold 42 is designed to provide output of each growth module 18 on an individual basis. Alternatively, the endpoints of the first and second bottom conduits 76 and 78 in the growth module 18 may be the outlet ports of the bottom manifold and may connect to the endpoints of other first and second bottom conduits from other growth modules in the system 10. In FIGS. 5 & 6, the endpoint of the first bottom conduit 76 that is on the same side of the growth module 18 connects to the corresponding endpoint of the second bottom conduit 78 on that side through a connecting piece 80. The end of the first bottom conduit 76 that is on the other side of the growth module 18 connects to the corresponding end of the second bottom conduit 78 on that side with a connecting piece 82 that is only partially shown in FIG. 6. Although only partially shown, the connecting piece 82 has the same structure as connecting piece 80. Preferably connecting pieces 80 and 82 extend between elbow joints 84 so that a rectangle is formed between the first bottom conduit 76, the second bottom conduit 78, and the connecting pieces 80 and 82.

Each of the connecting pieces 80 and 82 preferably has an outlet port configured as an outlet T-joint 86 disposed on it. The outlet T-joint 86 is centered between the connection of the first bottom conduit 76 and the second bottom conduit 78. The aligned openings of the outlet T-joint 86 face either the first or second bottom conduits 76 and 78 and the non-aligned opening of the outlet T-joint 86 faces away from the growth module 18. Preferably, there are two shutoff valves 88 in each of the connecting pieces 80 and 82 with one being located between the outlet T-joint 86 and the first bottom conduit 76 and the other being located between the outlet T-joint 86 and the second bottom conduit 78. Although the outlet T-joint 86 in each of the connecting pieces 80 and 82 could be located elsewhere, centering the outlet T-joint 86 promotes equal draining of the biomass/growth medium mixture during harvest. In addition, although a single outlet T-joint 86 could be used as the outlet port in the bottom manifold 42 two outlet T-joints are preferred for the same reason.

The non-aligned opening of each outlet T-joint 86 connects to a discharge manifold 90. As shown in FIG. 6, the discharge manifold 90 is configured to aggregate the collective output of the growth module 18 from each outlet T-joint 86 in the bottom manifold 42 when the collective harvest of each individual growth module 18 is desired; however, when the growth module 18 is connected to the bottom manifold 42 of other growth modules, the discharge manifold 90 may be configured to aggregate the collective output of the connected growth modules, as discussed infra.

Referring to the bottom manifold 42 in FIG. 6, the discharge manifold 90 extends from the non-aligned opening of each outlet T-joint 86 around half the perimeter of the rectangle formed by the first and second bottom conduits 76 and 78 and connecting pieces 80 and 82. The two sides of the discharge manifold 90 come together at a discharge T-joint 92 preferably at the center of the discharge manifold 90. The non-aligned opening of the discharge T-joint 92 connects to a discharge line 94. Referring back to FIG. 5, the discharge line 94 contains a discharge valve 96 and leads to a harvest tank 98 in the embodiment shown, however, the discharge line 94 could alternatively lead to a pipeline 100 (see FIG. 10) or elsewhere.

Similar to the individual growth column 16 discussed above, harvesting the biomass from the growth module 18 is preferably achieved through the effect of gravitational force on the biomass/growth medium mixture. Gravitational force on the biomass/growth medium mixture in the body 20 of each growth column 16 pulls the biomass/growth medium mixture downward toward the open bottom piece 38 of the growth column 16 into the bottom manifold 42. The bottom manifold 42 collects the biomass/growth medium mixture output from each growth column 16 in the growth module 18 and aggregates the growth columns' the collective output for transfer to the discharge manifold 90. The discharge manifold 90 collects the biomass/growth medium mixture output from the bottom manifold 42 and aggregates the bottom manifold's collective output for transfer to the discharge line 94.

How the bottom manifold 42 collects and aggregates the collective output of the biomass/growth medium mixture from the growth columns depends on the particular design of the bottom manifold 42. In the preferred bottom manifold 42, where the biomass/growth medium enters into the manifold depends on the location of the growth column 16 in the growth module 18. Gravity forces the biomass/growth medium mixture into either an upper T-joint 58 or an end T-joint 60. Gravitational force on the biomass/growth medium mixture in each growth column 16 above an upper T-joint 58 also forces biomass/growth medium mixture out of the manifold row 56 into the non-aligned opening of one of the end T-joints for that manifold row 56. Each end T-joint 60 receives biomass/growth medium mixture from both its respective manifold row 56 and the growth column 16 above that end T-joint 60. The biomass/growth medium mixture travels through the end T-joint 60, out of its downwardly facing aligned opening 66, and into the non-aligned opening of its corresponding lower T-joint 68. In the lower T-joint 68, the biomass/growth medium mixture is forced along the first and second bottom conduits 76 and 78 and into one of the connecting pieces 80 and 82. In the connecting pieces 80 and 82, the biomass/growth medium mixture is forced into and out of the outlet T-joint 86 to the discharge manifold 90 for transfer to the discharge line 94.

Initiating flow of the biomass/growth medium mixture from the growth module 18 to its ultimate destination is controlled by one or more valves located downstream from the flow of the biomass/growth medium mixture (e.g., the discharge valve 96, the shut-off valves 88, etc.). When the downstream valve is opened the biomass/growth medium mixture flows out of the growth module 18. Preferably, gravitational force alone drives the flow of the biomass/ growth fluid mixture from the growth module 18 to its ultimate destination; however, this flow may be aided by other forces (e.g., pumps) if necessary.

When harvesting, it has been found that approximately ten to thirty percent of the biomass/liquid growth medium mixture is preferably removed from each growth column 16. Although the configuration of the growth module 18 would allow all of the biomass/growth medium mixture to be removed from the growth columns, such a result is not desired. Instead, the portion of the biomass/growth medium mixture removed from each tube is replenished with additional liquid growth medium and/or biomass/liquid growth medium mixture and the remaining biomass/growth medium mixture in the growth columns after harvest regenerates quicker and there is less of a lag time between harvests.

Figure 7:
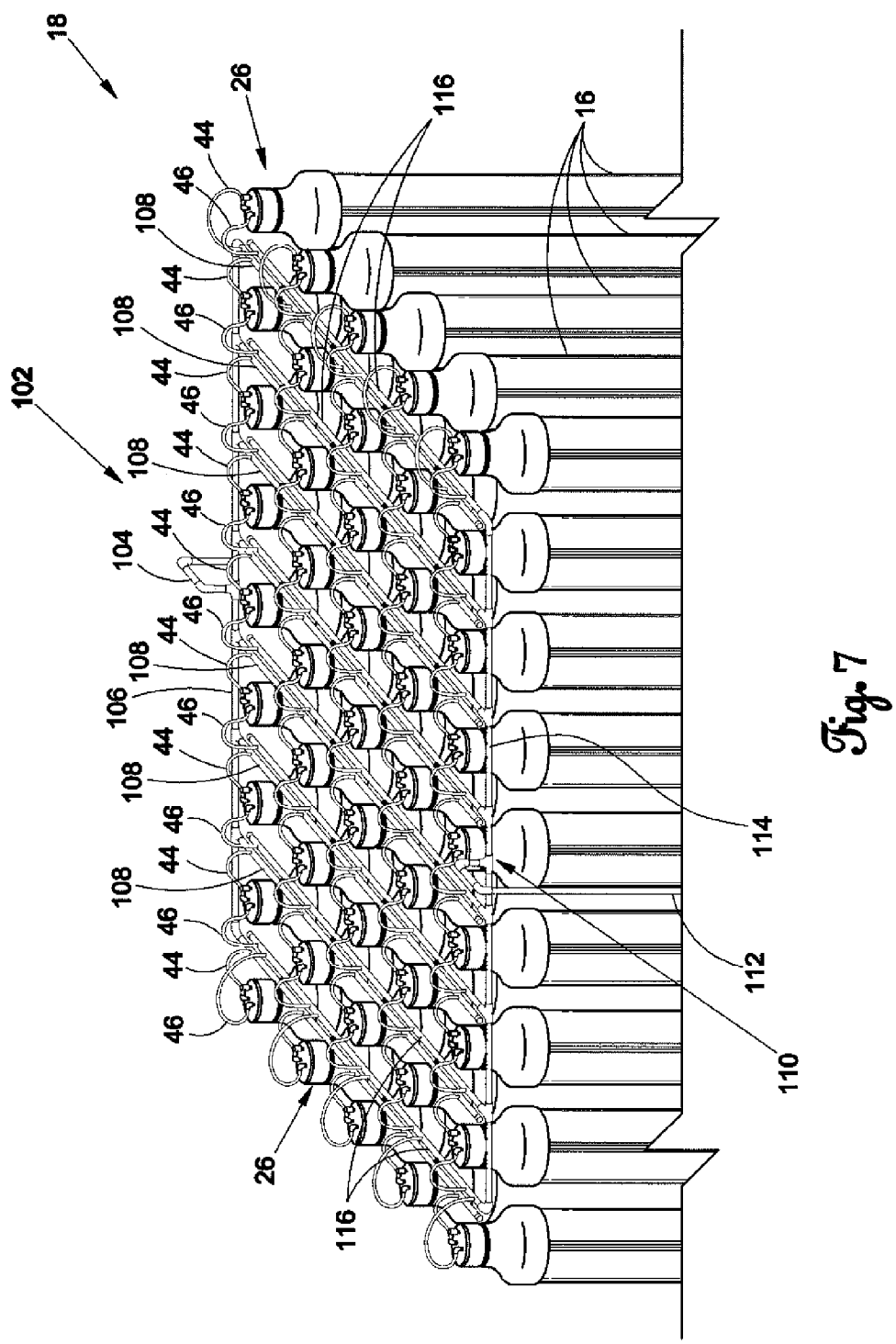
FIG. 7 is an enlarged view of the top portion of the growth module depicted in FIG. 5 and shows the preferred embodiment of a nutrient delivery manifold and a gas delivery manifold.

Turning now to FIG. 7, the top of the preferred growth module 18 is shown. As previously discussed, the top piece 26 of each growth column 16 has the gas delivery line 44 and the nutrient delivery line 46 protruding from it. With forty-five growth columns in the preferred growth module 18 there are forty-five gas delivery lines and forty-five nutrient delivery lines per growth module 18. Each gas delivery line 44 in the growth module 18 connects to a gas delivery manifold 102 that preferably extends through the growth module 18 near the top piece 26 of each growth column 16. The gas delivery manifold 102 is connected to a gas input line 104 from a gas source (not shown) and connects to the gas delivery line 44 of each growth column 16 in the growth module 18.

Figure 8:
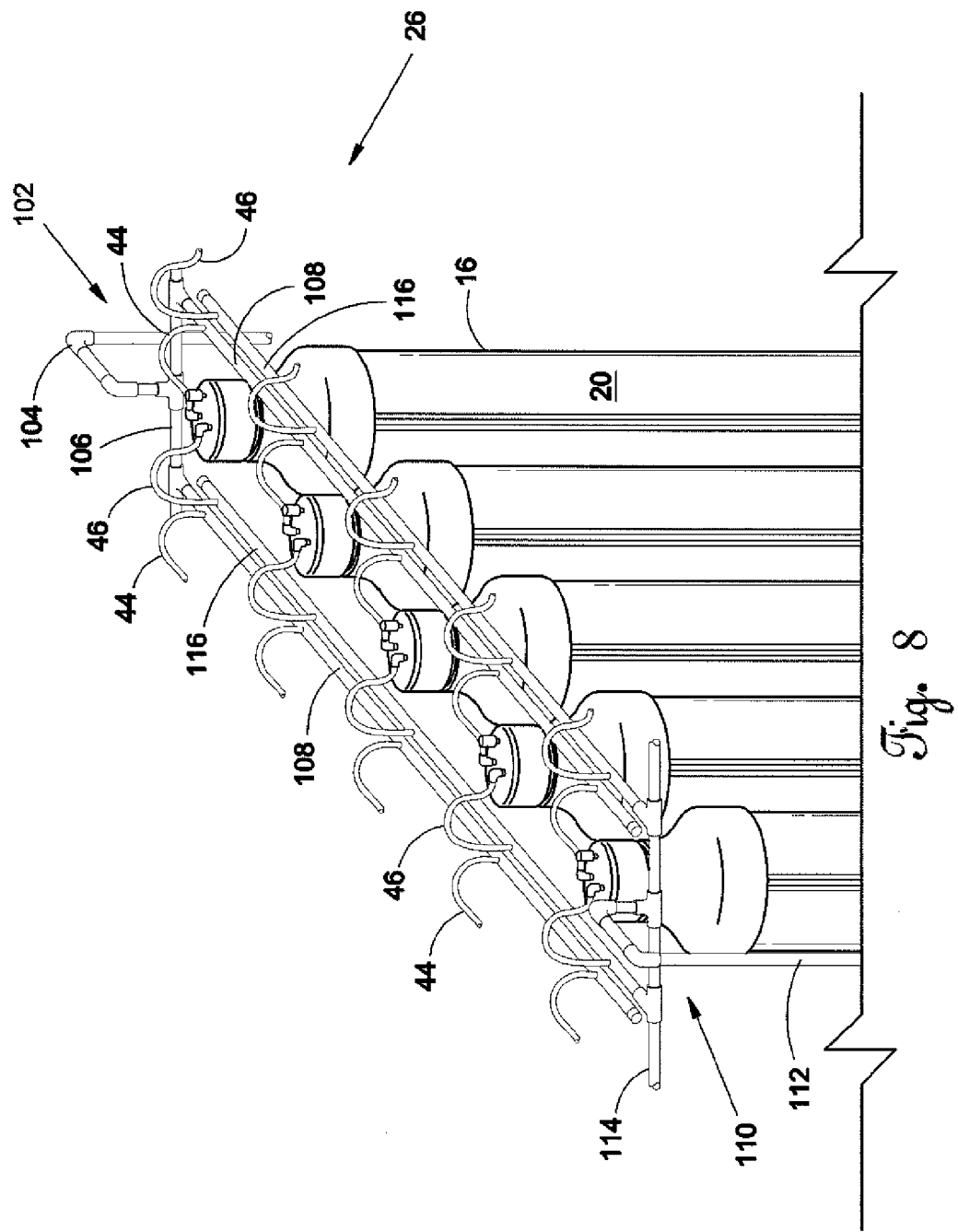
FIG. 8 is an enlarge cutaway view of the nutrient delivery manifold and the gas delivery manifold show in FIG. 7

A portion of the preferred gas delivery manifold 102 from FIG. 7 is cut away and shown in FIG. 8. As shown in FIGS. 7 & 8, the preferred gas delivery manifold 102 has a gas baseline 106 extending along one side of the growth module 18, at or near the top of the growth module 18. The gas input line 104 connects to the gas baseline 106 at the midpoint of the gas baseline 106. Gas delivery branches 108 connect to the gas baseline 106 at various points and extend in a straight line from the gas baseline 106 toward the opposite side of the growth module 18, between the top pieces of the growth columns. As such, the gas delivery branches 108 are parallel to each other.

In the preferred gas delivery manifold 102, the gas input line 104 brings gas from a gas source (not shown) to the gas baseline 106. The gas travels from the gas baseline 106, through the gas delivery branches 108, to the gas delivery line 44 of each growth column 16 and ultimately to the biomass/growth medium mixture therein. It should be noted that the gas source can be a permanent or temporary storage medium (e.g., a tank) or gas could be piped in directly from a gas producing source (e.g., $CO_2$ segregated from coal-fired power plant emissions introduced directly to the gas input line 104). In addition, multiple gas input lines could be connected to the gas delivery manifold 102.

Similar to the gas delivery lines, the nutrient delivery line 46 of each growth column 16 connects to a nutrient delivery manifold 110 that preferably extends through the growth module 18 near the top piece 26 of each growth column 16. The nutrient delivery manifold 110 is connected to a nutrient input line 112 from a source (not shown) and connected to the nutrient delivery line 46 of each growth column 14 in the growth module 18.

The preferred nutrient delivery manifold 110 is similar in form to the preferred gas delivery manifold 102 and a cutaway portion from FIG. 7 is shown in FIG. 8. The preferred nutrient delivery manifold 110 has a nutrient baseline 114 extending along one side of the growth module 18, at or near the top of the growth module 18. Preferably, the nutrient baseline 114 extends along the side of the growth module 18 opposite the side of the growth module 18 where the gas baseline 106 extends. The nutrient input line 112 connects to the nutrient baseline 114 at the midpoint of the nutrient baseline 114. Nutrient delivery branches 116 connect to the nutrient baseline 114 at various points and extend in a straight line from the nutrient baseline 114 toward the opposite side of the growth module 18, between the top pieces of the growth columns. As such, the nutrient delivery branches 116 are parallel to each other in the preferred growth module 18.

In the preferred nutrient delivery manifold 110, the nutrient input line 112 brings liquid-based materials from the source (not shown) to the nutrient baseline 114. The liquid-based materials travel from the nutrient baseline 114, through the nutrient delivery branches 116, to the nutrient delivery line 46 of each individual growth column 16 and ultimately to the biomass/growth medium mixture therein. The source for the nutrient input line 112 can be a permanent or temporary storage medium or the liquid-based materials could be piped in directly from a source that produces the desired liquid-based materials. In addition, multiple nutrient input lines could be connected to nutrient delivery manifold 110.

Now that preferred growth module 18 has been explained the importance of the friction fit discussed supra should become apparent when one considers the necessity of repair. If, for example, the body 20 of one growth column 16 in the growth module 18 is damaged and has to be replaced, the disconnectability of the friction fit facilitates repair. If the connection between the damaged body 20 and the bottom piece 38 (see FIG. 4) were glued or otherwise permanently affixed, the damaged body 20 of the growth column 16 could not be disconnected and alternative measures for repair would be required. On the other hand, the damaged body 20 in the preferred growth column 16 with the friction fit could be easily removed from the bottom piece 38. The same rationale applies to repair of other damaged components in the growth module 18 which connect with the friction fit.

As mentioned, the growth module 18 may be one of many in the system 10. It is envisioned that large-scale biomass growing systems will have one or more growth modules partially surrounded by the shading element 14, as shown for example in FIG. 1.

In the system 10, the shading element 14 at least partially surrounds, but does not necessarily touch, one or more growth columns and in large-scale biomass growing operations one or more growth modules. Preferably, the shading element 14 partially surrounds the growth column 16 or the growth module 18 such that sunlight must pass through the shading element 14 prior to contacting the growth column 14 or growth module 18 for the majority of daylight hours.

The shading element 14 is the material covering the tops and sides of the preferred structure 12 shown in FIG. 1, not the structure 12 itself. The structure 12 supports the shading element 14. Any number of structures, other than that shown in FIG. 1, could support the shading element 14 and hold it in relation to the growth columns and/or growth modules. For example, the shading element 14 could be supported and held by posts so that the overall structure resembles more of a tent-like structure.

The shading element 14 is made from any material that diffuses direct sunlight. In the preferred embodiment, the shading element 14 is formed from a weave of white polypropylene material that has been treated with an ultraviolet stabilizer to resist UV degradation. The weave is constructed with a flat warp and a round pick, with the flat warp being woven over and under the round pick. Weaving the flat warp over and under the round pick causes peaks and valleys in the flat warp. Direct sunlight hits peaks and valleys of the warp and is partially reflected, partially absorbed, and partially transmitted through the shading element 14. The sunlight that passes through (i.e., transmitted) is scattered in all different directions, thereby eliminating all shadows on the side of the shading element 14 opposite the sun.

The elimination of shadows by the shading element 14 promotes uniform light delivery to the biomass in the growth column 16. In this regard, the back side of the growth column 16 is not shaded off by the side of the growth column 16 facing toward the sun. In addition, as it applies to the growth module 18, the growth columns at the interior of the growth module 18 are not shaded off by the outer growth columns closer toward the sun.

The diffuse light from the shading element 14 also promotes photosynthesis of the biomass at all depths of the growth column 16, thereby increasing the yield attained by the system 10. In this regard, the biomass receives similar amounts of diffused light regardless of location of the biomass in the growth column 16. Moreover, light diffusion by the shading element 14 increases the photosynthetic efficiency of the biomass by reducing photoinhibition. Photoinhibition occurs when certain proteins involved in the photosynthetic process are damaged, for example by direct sunlight, and normal photosynthetic processes are reduced.

Figure 9:
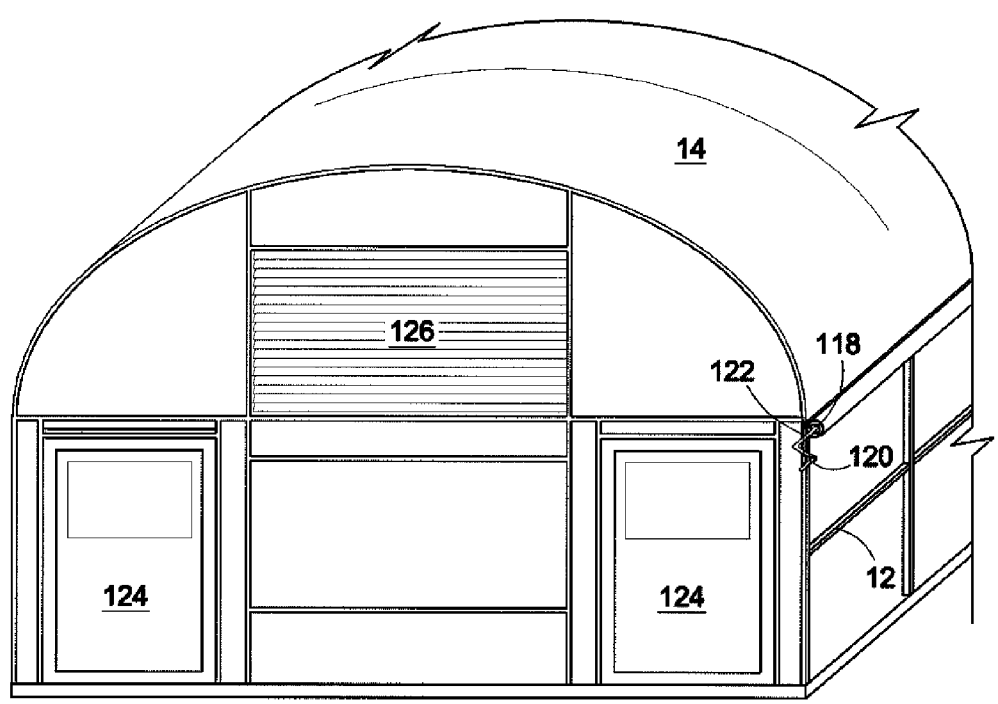
FIG. 9 is an enlarged cutaway view of the system in FIG. 1 showing the shading element rolled up on one side of the structure supporting it.

FIG. 9 shows a portion of the preferred structure 12 and illustrates a component that is preferably present in the system 10. As shown, a portion of the shading element 14 extending from one side of the structure 12 has been rolled up around a crankshaft 118. The crankshaft 118 extends along the bottom edge of the shading element 14 when the shading element 14 is unrolled. The crankshaft 118 has a handle 120 at both of its ends and the applicable portion of the shading element 14 is rolled from the ground up by turning the handle 120 at each end. Once this portion of the shading element 14 is rolled up, the handle 120 is secured to the building with a rope 122 or some other fastening device. The shading element can be rolled up in this manner to provide ventilation. In addition, FIG. 9 shows a door 124 and a vent 126 that are also present on the preferred structure 12.

Figure 10:
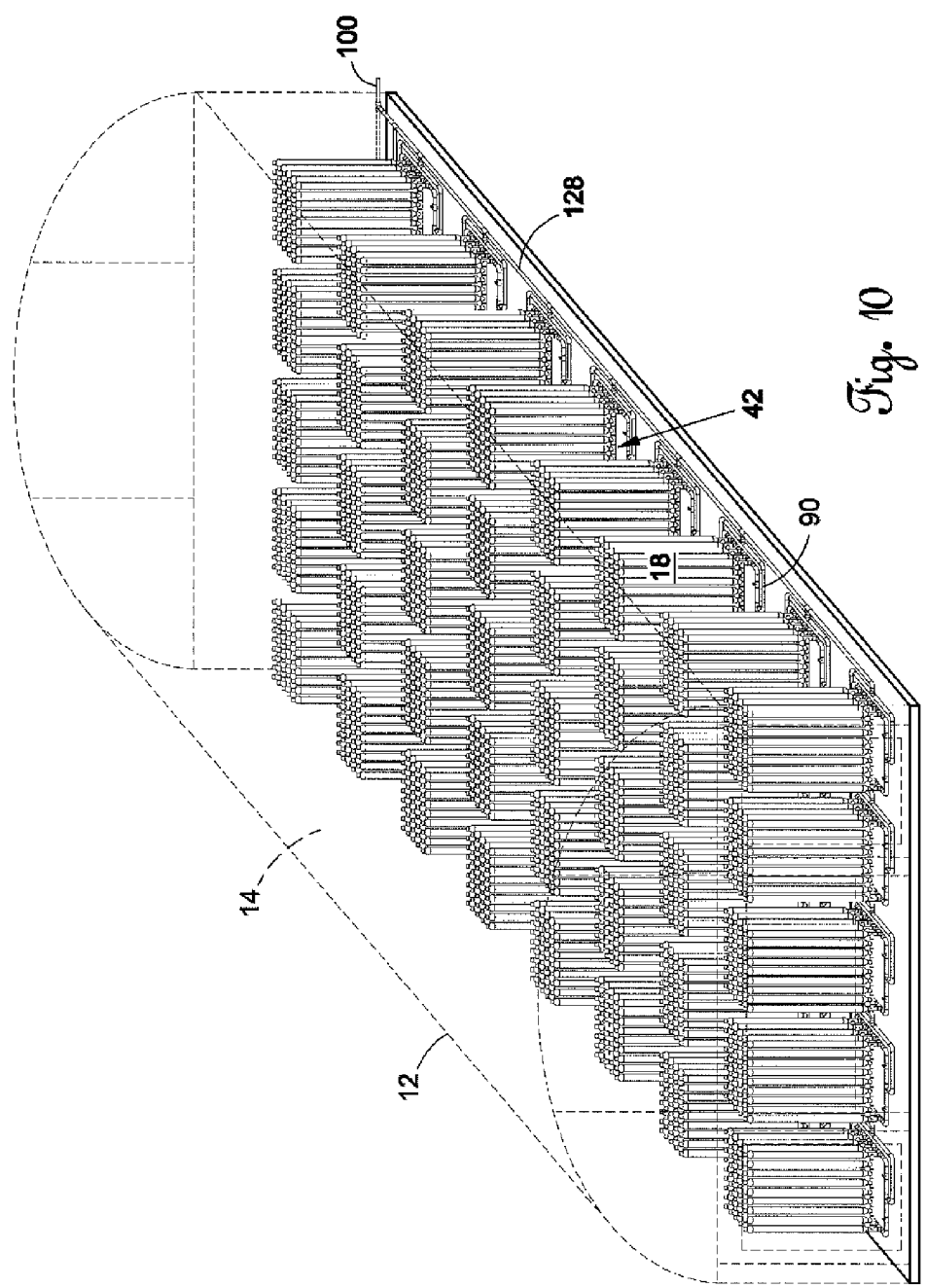
FIG. 10 is a perspective view of the system with the shading element and a portion of the structure supporting said shading element removed.

Within the diffused light of the shading element 14, the arrangement and number of growth columns and/or growth modules in the system 10 is a design choice. FIGS. 1 & 10, which have a portion of the shading element 14 and a portion of the preferred structure 12 removed for illustration purposes, show two possible arrangements of growth modules in the system 10. In FIG. 1, the numerous growth modules individually connect to a common discharge line 128 through their bottom manifold 90 and the common discharge line 128 feeds into the single harvest tank 98 in the system 10. Alternatively, the numerous growth modules in FIG. 1 could each have its own harvest tank 98 as in FIG. 5. As shown in FIG. 10, the numerous growth modules individually connect to the common discharge line 128 through their bottom manifold 90 and the common discharge line 128 connects to the pipeline 100 outside the structure 12.

Another possible arrangement of growth modules in the system 10 is to connect them as a chain (not shown) with one or more growth modules linked via their bottom conduits. In this regard, an endpoint of the first and second bottom conduits 76 and 78 of one growth module 18 (see FIG. 6) are connected to a corresponding endpoint of the first and second bottom conduit 76 and 78 of an adjacent growth module 18. Any number of growth modules could be linked in this way and the discharge manifold 90 would collect and aggregate the collective output of all the growth modules in the chain, for delivery of the collective output of the chain to the discharge line 94. In this regard, the outermost endpoints of the first and second bottom conduits 76 and 78 of the first growth module 18 in the chain could be connected with the connecting piece 80 (see FIG. 6) and the outermost endpoints of the first and second bottom conduits 76 and 78 of the last growth module 18 in the chain could be connected with the connecting piece 82 (see FIG. 6). The discharge manifold 90 would connect to the outlet port (i.e., outlet T-joint 86) of the connecting pieces 80 and 82 to aggregate the collective output of the chain of growth modules. Again, the discharge line 94 would then deliver the collective output of the chain to a desired location such as the harvest tank 98, the pipeline 100, or elsewhere.

Alternatively, each growth module 18 in the chain of growth modules could be connected such that a single outlet port (e.g., outlet T-joint 86 in FIG. 6) connects to the a corresponding single outlet port of the adjacent growth module 18.

Figure 11:
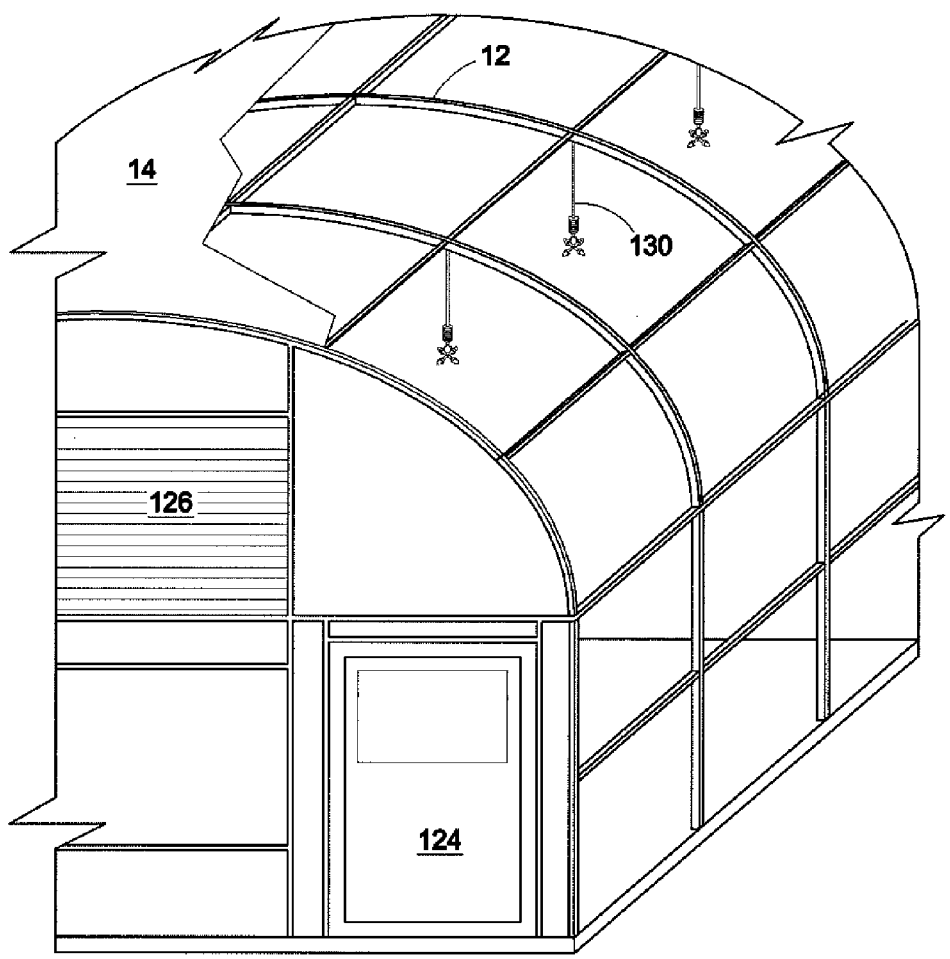
FIG. 11 is an enlarged cutaway view of the system with a portion of the shading element removed.

FIG. 11 shows the same portion of the preferred structure 12 in FIG. 9; however, a portion of the shading element 14 has been removed to reveal additional components of the system 10 which may be present. As shown, a temperature control system 130 is in place under the removed portion of the shading element 14. The temperature control system 130 regulates the temperature surrounding the growth columns by misting groundwater or some other type of non-toxic liquid into the environment around and on the growth columns. The temperature surrounding the growth columns either rises or fall based upon the temperature of the liquid coming from the temperature control system 130.

The temperature of the environment surrounding the growth columns affects the interior temperature of the growth column 16 and the production rate of the biomass therein. The biomass and/or the growth column 16 can be negatively affected if the temperature gets too hot or too cold within the system 10. For example, freezing temperatures can kill some types of biomass or even worse yet, may cause failure of the growth column 16 if the liquid growth medium freezes and expands to a point that fractures the growth column 16. Conversely, if the temperature of the growth column gets too hot the biomass may denature and not be able to perform vital metabolic processes.

If has been found that the preferred biomass can be grown in temperatures ranging from approximately 14° Celsius to 32° Celsius; however, the temperature optimally should be kept between 20° Celsius and 30° Celsius. To maintain optimal growing temperatures, a temperature feedback mechanism (not shown) is preferably in place within the system 10. The temperature feedback mechanism is coupled to a thermometer (not shown) that provides real-time measurement of the temperature. The thermometer may be positioned to measure (1) the temperature of the biomass/growth medium mixture within the growth column 16; (2) the temperature of the environment around the growth column 16; or, (3) the temperature of both. The temperature control system 130 is preferably automated so that it activates based on the data from the temperature feedback system however it could be manually activated.

Concerning automation, it should be noted that other processes within the preferred system 10 are automated through multiple feedback systems (not shown) controlled by a processor (not shown). The processor receives and processes real-time data from sensors within the system 10 and controls the operation of various functions within the system based on that information. For example, the delivery of $CO_2$ can be controlled by real-time feedback of information about the pH level within the growth column 16 as discussed supra. Other examples of automation are activation of the temperature control system 130 based on input from thermometers as well as the delivery of nutrients based on real-time testing of nutrient composition within the growth column 16.

As for automated harvesting of the biomass/growth medium mixture, this can be initiated by electronically-operated valves which open at preset times, according to known growth rates of the biomass. The amount of biomass/growth medium mixture extracted from the growth column 16 is also preferably controlled via a feedback system, with feedback coming from sensors within the growth column 16 that measure the fluid level of biomass/growth medium mixture in the growth column 16. Once the biomass/growth medium mixture gets to a certain point in the growth column 16, the sensors notify the processor and the processor tells the electronically-operated downstream valves to close. The processor then instructs one or more valves (not shown) to be opened and the nutrient delivery line 46 re-inoculates the growth column 16 with the proper amount and percentage biomass/growth medium mixture.

Finally, although not shown in FIG. 11, artificial lights could also be present in the system 10 to provide increased light for growth of the biomass. Artificial lighting can be used to increase the exposure of the biomass to light that is otherwise not available naturally as, for example, during winter months when daylight is shortened. Increased exposure to light promotes photosynthesis and ultimately increases yield. As with the other systems above, light delivery of artificial light may be on a preset schedule controlled by the processor or could also be part of an automated system that relies on feedback from light sensors.

On a global scale, it is anticipated that numerous biomass growing systems would be arranged on a piece of land so that the entire site is dedicated to the production of biomass (see FIG. 1). Preferably, the biomass growing systems would be arranged on the site so that the greatest number of systems fit on the site, thereby optimizing the production of biomass. For example, the biomass growing systems on the site could be arranged into a grid pattern which allows the site operator to efficiently move between the systems.

The pipeline 100 would extend through the site and each of the biomass growing systems would feed into the pipeline 100 with a check valve (not shown) present between the pipeline 100 and the system 10. Preferably, the pipeline 100 would be pressurized and once biomass/growth medium is output to it, the pressure gradient forces the biomass/growth medium mixture to a desired location. Alternatively, the pipeline 100 may be flushed with additional liquid growth medium or another liquid to transport the biomass/growth medium mixture to a desired location.

Although the present invention has been described with reference to specific embodiments, this description is not meant to be construed in a limiting sense. Various modifications of the disclosed embodiments, as well as alternative embodiments of the invention will become apparent to persons skilled in the art upon the reference to the above description of the invention. It is, therefore, contemplated that the appended claims will cover such modifications that fall within the scope of the invention.

We claim:

1. A system for growing biomass in a liquid growth medium, said system comprising at least one growth module consisting of:
    a plurality of individual, spaced, hollow, tubular growth columns each extending substantially vertical, and extending parallel to each other, each tubular growth column being made from a material for allowing light to pass therethrough;
    a bottom manifold connected to each of said growth columns, said bottom manifold being configured for receiving gravity induced output flowing vertically downwardly from each of said growth columns for aggregating said output into a collective output of said growth module; and,
    at least one outlet port disposed on said bottom manifold;
    at least one valve in fluid communication with said at least one outlet port of said growth module,
    said at least one growth module including a gas delivery manifold connected to a gas input line, said gas delivery manifold having outlet ports connected to a gas delivery line that extends into the interior of each of said growth columns for delivering at least one gas into said growth columns for allowing said gas to migrate vertically upwardly through said growth columns; and
    a shading structure spaced from and at least partially surrounding said at least one growth module, said shading structure being configured for defusing light which passes therethrough.

2. The system of claim 1 wherein said shading structure is located relative to said at least one growth module such that sunlight must pass through at least a portion of said shading structure prior to contacting said at least one growth module for the majority of daylight hours.

3. The system of claim 1 wherein said at least one growth module comprises a plurality of growth modules and said shading structure at least partially surrounds said plurality of growth modules.

4. The system of claim 3 wherein said at least one outlet port of each bottom manifold connects to a common discharge line extending among said plurality of growth modules.

5. The system of claim 4 wherein said common discharge line selectively feeds into a harvest tank or a pipeline.

6. The system of claim 1 comprising a plurality of fluidly connected growth modules having at least one outlet port of each growth module being connected to a corresponding outlet port of an adjacent growth module.

7. The system of claim 6 wherein an at least one secondary outlet port of each growth module is connected to a corresponding secondary outlet port of said adjacent growth module.

8. The system of claim 7 wherein said plurality of fluidly connected growth modules form a chain of growth modules, said chain of growth modules terminating with a first growth module and a last growth module, and wherein a discharge manifold fluidly connects at least one outer outlet port disposed on said bottom manifold of said first growth module to an outer outlet port disposed on said bottom manifold of said last growth module.

9. The system of claim 1 wherein said at least one growth module includes a nutrient delivery manifold connected to a nutrient input line, said nutrient delivery manifold having outlet ports connected to a nutrient delivery line that extends from the interior of each of said growth columns.

10. The system of claim 1 including a temperature control system disposed on said structure, said temperature control system comprising a plurality of fluid misting devices connected to an activation mechanism.

11. The system of claim 1 comprising an artificial lighting system, said artificial lighting system comprising a plurality of artificial lights connected to an activation mechanism.

12. The system of claim 1 wherein said shading structure includes an ultraviolet stabilizer for reducing passage of ultraviolet light therethrough.

13. The system of claim 1 wherein said at least one growth module includes a nutrient delivery manifold connected to a nutrient input line, said nutrient delivery manifold having outlet ports connected to a nutrient delivery line that extends from the interior of each of said growth columns, and said nutrient input line introduces nutrient for vertical migration within said vertically disposed growth columns.

\* \* \* \* \*